(12) United States Patent
Watanabe et al.

(10) Patent No.: US 7,960,168 B2
(45) Date of Patent: Jun. 14, 2011

(54) BIOLOGICALLY ACTIVE SUBSTANCE TRANSFER SHEET, CELL CULTURE KIT CONSTITUTED OF CELL CULTURE PLATE AND BIOLOGICALLY ACTIVE SUBSTANCE TRANSFER SHEET, PRODUCING METHOD THEREOF AND METHOD FOR SCREENING CELL CULTURE CONDITIONS UTILIZING THE SAME

(75) Inventors: Kohei Watanabe, Tokyo (JP); Takeshi Miyazaki, Yokohama (JP); Osamu Kanome, Yokohama (JP); Ryoichi Matsuda, Tokyo (JP); Tomoyo Fujiyama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 21 days.

(21) Appl. No.: 12/183,008

(22) Filed: Jul. 30, 2008

(65) Prior Publication Data

US 2008/0293138 A1 Nov. 27, 2008

Related U.S. Application Data

(62) Division of application No. 10/554,211, filed as application No. PCT/JP2004/019289 on Dec. 16, 2004, now Pat. No. 7,419,820.

(30) Foreign Application Priority Data

Dec. 16, 2003 (JP) ................. 2003-418523
Dec. 16, 2003 (JP) ................. 2003-418535

(51) Int. Cl.
    *C12M 1/34* (2006.01)
(52) U.S. Cl. .................................... 435/287.1
(58) Field of Classification Search .......................... None
    See application file for complete search history.

(56) References Cited

U.S. PATENT DOCUMENTS

| 3,031,819 | A | 5/1962 | Menolasino et al. |
|---|---|---|---|
| 5,108,926 | A | 4/1992 | Klebe |
| 5,370,842 | A | 12/1994 | Miyazaki et al. |
| 5,380,490 | A | 1/1995 | Hoshi et al. |
| 5,512,446 | A | 4/1996 | Miyazaki et al. |
| 5,534,441 | A | 7/1996 | Miyazaki et al. |
| 5,601,983 | A | 2/1997 | Takayama et al. |
| 5,624,798 | A | 4/1997 | Yamamoto et al. |
| 5,670,315 | A | 9/1997 | Yamamoto et al. |
| 5,679,516 | A | 10/1997 | Okamoto et al. |
| 5,679,581 | A | 10/1997 | Miyazaki et al. |
| 5,700,647 | A | 12/1997 | Miyazaki et al. |
| 5,846,730 | A | 12/1998 | Miyazaki et al. |
| 6,022,961 | A | 2/2000 | Yamamoto et al. |
| 6,103,479 | A | 8/2000 | Taylor |
| 6,124,138 | A | 9/2000 | Woudenberg et al. |
| 6,232,066 | B1 | 5/2001 | Felder et al. |
| 6,368,838 | B1 | 4/2002 | Singhvi et al. |
| 2002/0019011 | A1 | 2/2002 | Stockwell et al. |
| 2002/0177221 | A1 | 11/2002 | Nishiguchi et al. |
| 2002/0182721 | A1 | 12/2002 | Nishiguchi et al. |
| 2006/0246508 | A1 | 11/2006 | Watanabe et al. |

FOREIGN PATENT DOCUMENTS

| EP | 0 889 751 | 1/1999 |
|---|---|---|
| EP | 1 248 108 | 10/2002 |
| EP | 1 253 196 | 10/2002 |
| JP | 2000-508528 | 7/2000 |
| JP | 2000-512009 | 9/2000 |
| JP | 2002-328124 | 11/2002 |
| JP | 2002-355025 | 12/2002 |
| JP | 2002-355026 | 12/2002 |
| JP | 2003-33177 | 2/2003 |
| JP | 2003-504011 | 2/2003 |
| WO | 97/36681 | 10/1997 |
| WO | 97/45730 | 12/1997 |
| WO | 98-43123 | 10/1998 |
| WO | 99/32663 | 7/1999 |

OTHER PUBLICATIONS

Vrouwenvelder et al. "Better histology and biochemistry for osteoblasts cultured on titanium-doped bioactive glass: Bioglass 45S5 compared with iron-, titanium-, fluorine- and boron-containing bioactive glasses", Biomaterials, 1994, 15(2):97-106.*
Schroeder et al. "Titanium containing amorphous hydrogenated carbon films (a-C:H/Ti): surface analysis and evaluation of cellular reactions using bone marrow cell cultures in vitro", Biomaterials, 2000, 21:449-456.*
Ma et al. "A preliminary in vitro study on the fabrication and tissue engineering applications of a novel chitosan bilayer material as a scaffold of human neofetal dermal fibroblasts", Biomaterials, 2001, 22:331-336.*
Hyun et al. "Micropatterns of a cell-adhesive peptide on an amphiphilic comb polymer film", Langmuir, 2002, 18:2975-2979.*
Cagri et al. "Antimicrobial, mechanical, and moisture barrier properties of low pH whey protein-based edible films containing p-Aminobenzoic or sorbic acids", Journal of Food Science, 2001, 66(6):865-870.*
Padgett et al. "Incorporation of food-grade antimicrobial compound into biodegradable packaging films", Journal of Food Protection, 1998, 61(10):1330-1335.*
Yoshihiro Ito, "Biomaterial to Communicate with Cells: Adhesion and Gene Expression of Cells", Protein Nucleic Acid and Enzyme, vol. 45, No. 5, 2000, pp. 727-734.
Elizabeth Smith, et al., "Monoclonal Antibody Screening: Two Methods Using Antigens Immobilized on Nitrocellulose", Analytical Biochemistry, vol. 138, 1984, pp. 119-184.

* cited by examiner

*Primary Examiner* — Jon P Weber
*Assistant Examiner* — Bin Shen
(74) *Attorney, Agent, or Firm* — Fitzpatrick, Cella, Harper & Scinto

(57) ABSTRACT

The invention provides a biologically active substance transfer sheet which can be formed with simple steps, a cell culture kit which comprises a cell culture plate and a biologically active substance transfer sheet, a producing method therefor, and a method for screening cell culture conditions with cells. The transfer sheet is prepared by providing biologically active substances having biological activity in plural areas on a sheet base, and biologically active substances are supplied from the sheet to culture regions provided on the plate.

12 Claims, 6 Drawing Sheets

BIOLOGICALLY ACTIVE SUBSTANCE TRANSFER SHEET, CELL CULTURE KIT CONSTITUTED OF CELL CULTURE PLATE AND BIOLOGICALLY ACTIVE SUBSTANCE TRANSFER SHEET, PRODUCING METHOD THEREOF AND METHOD FOR SCREENING CELL CULTURE CONDITIONS UTILIZING THE SAME

This application is a divisional of application Ser. No. 10/554,211, which was the National Stage of International Application No. PCT/JP2004/019289, filed Dec. 16, 2004. The contents of each of the foregoing applications is incorporated herein by reference.

TECHNICAL FIELD

The present invention relates to a sheet for transfer one or more biologically active substances being physiologically active to a certain cell, which sheet is usable for identifying their functions or the effect of combinations of two or more biologically active substances or for screening biologically active substances utilizing cells. The present invention also relates to a cell culture kit constituted of at least a cell culture plate and the above biologically active substance transfer sheet, a producing method thereof and a method for screening cell culture conditions utilizing the same.

BACKGROUND ART

In recent years, studies of culturing animal or plant cells under various conditions and studies of products of cultured cells have been actively carried out. Particularly, studies on production of substances, of which artificial synthesis is impossible or very difficult, utilizing certain cell activities are carried out in various fields. Also studies are carried out to identify substances that affect cellular growth and differentiation so as to obtain proliferation or differentiation of certain cells with them according to the purpose. Also with the rapid progress in cell engineering and medical engineering, minute biosensors, artificial organs, neurocomputers and the like are attracting attentions and actively studied.

In order to utilize cells in vitro as explained above, it is essential to dispose cells to control their proliferation, differentiation and substance production in a desired manner. However, the mechanisms of cell disposition, cell proliferation and differentiation, and substance production have not been sufficiently clarified, so that the cell culture under controlled conditions is extremely difficult impeding researches utilizing cells.

Also tailor-made therapy considering individual difference in the sensitivity to drugs, of which concept has recently been widely recognized, is strongly desired, but the influence of biologically active substances has been investigated on the function of respective substances, particularly because of technical reasons, and there has not been established an effective method of easily investigating presence/absence of effects of plural drugs, or a required dose thereof or a combined effect thereof.

As an attempt to control cell disposition, U.S. Pat. No. 6,368,838 discloses a method for culturing cells by forming a pattern of cell adhesive portions on a substrate to control arrangement of cells of plural species. U.S. Pat. No. 5,108,926 also describes formation of a pattern on a substrate by applying a cell-adhering protein using an ink jet printer and cell culture thereon. These methods allow to culture cells on the formed pattern of the cell-adhering protein, but not to control the proliferation, differentiation and substance production of the cells or to achieve screening of cell culture conditions. Also "Protein, Nucleic acid and Enzyme", vol. 45, 727-734 (2000) describes immobilization of a cell growth factor, which affects cell proliferation or differentiation, on a substrate using photolithography, thereby investigating its influence on the cell proliferation and differentiation. However, the substrate on which the cell growth factor is immobilized is not used for screening, and the photolithography has problems that a rare biological substance is wasted and the production process is complicated requiring repetition of exposure and development steps.

Japanese translation of PCT international application No. 2000-512009 proposes a cell screening method by immobilizing onto a substrate a substance that affects cell adhesion. In this method, reactive functional groups provided on the substrate and the cell-adhering substance are bonded through a divalent crosslinking reagent, and photolithographic technology is used to bond the reactive functional group and the cell-adhering substance. However it has a problem, in addition to the aforementioned problems, that when plural cell-adhering substances are immobilized, it is extremely difficult to avoid a situation that an already immobilized substance and a substance to be newly immobilized are bonded by the divalent crosslinking reagent in undesired positions, that is, it is extremely difficult to arrange cell-adhering substances in desired positions. Also the proposed method is not to immobilize a substance influencing the cell proliferation, differentiation and substance production. That method is to screen cells by immobilizing cells in individual wells through the immobilized adhering substance, culturing the cells in a culture medium and detecting a certain substance produced by the cells. Thus it is not intended for screening a substance which influences at least one of adhesive property, proliferation, differentiation, survival, maintenance of an undifferentiated state, death and material production of cells, as intended in the present invention.

U.S. Pat. No. 6,103,479 discloses a method that allows effective confirmation of effects of a physiologically active substance using cells, where different cells are immobilized on a substrate to form an array to which an physiologically active substance is applied. This method, however, does not consider immobilization of physiologically active substances onto a substrate. This method requires a microfluidic delivery system to delivery the physiologically active substance to the substrate, and when plural physiologically active substances are used, complicated operations are required to load them onto the apparatus.

Also Japanese Patent Application Laid-open No. 2002-355025 discloses a method of forming a screening substrate characterized in immobilizing plural screening substances by using liquid discharge means in desired areas of a base, thereby providing different screening functions. In this invention, since the substances for screening are immobilized to the screening substrate, cells often cannot intake the screening substance into the cells. Therefore, this invention is not effective in the case where only the screening substance taken into the cells can affect at least one of the cellular functions including proliferation, differentiation, survival, maintenance of an undifferentiated state, death and substance production.

Also Japanese Patent Application Laid-open No. 2002-328124 discloses a screening method with a higher order combination of biological active substances, but this is to evaluate an effect of a function of biological active substances provided to a substrate, so it cannot be used for screening effects of biological active substances that function in vivo in a state immobilized on the extracellular matrix, or an effect induced by successive addition of biological active substances.

Also Japanese Patent Application Laid-open No. 2003-33177 proposes a simple assay of chemical substances such as drugs or toxic substances, preparing a cell array divided into plural areas and providing a biologically active substance to each area to carry out simultaneous screening of plural samples. In such a method, however, each biologically active substance is provided to the cultured cells by using a dispensing means. Thus there is a risk of contamination in the dispensing step and it requires a specific apparatus for dispensing the biologically active substances, far from convenient use.

DISCLOSURE OF INVENTION

In consideration of the foregoing, the present invention aims to provide a sheet for transfer one or more biologically active substances and a cell culture kit using it which can solve the technical problems in the aforementioned prior techniques and enable simultaneous evaluation of the effects of plural biologically active substances in an immobilized or dissolved state through simple steps, as well as a producing method of such a sheet and a screening method utilizing the same, thereby providing a basic technology for further advance in cell engineering and for various cell-utilizing devices. Another object of the present invention is to provide a screening method utilizing such a cell culture kit, for screening a substance which influences at least one of all the biological activities of a cell. Still another object of the invention is to provide a method of screening a biologically active substance utilizing cells.

Still another object of the present invention is to provide a method useful in screening of a biologically active substance which influences cell functions, at least one of proliferation, differentiation, survival, maintenance of an undifferentiated state, death and substance production, only when it is taken into cells, or a method useful in determining effects of successive addition of one or more biologically active substances.

The present invention provides a biologically active substance transfer sheet (hereinafter referred to as a transfer sheet) including the following embodiments:

(1) A transfer sheet that transfers a biologically active substance to a culture region on a culture plate when placed on the culture plate, the sheet which comprises a sheet base; and a holding area provided on the sheet base, the area holding at least one substance having a biological activity to a cell; wherein the holding area is provided in a position for covering the culture region of the culture plate.
(2) The transfer sheet of the above (1), wherein the biologically active substance is releasable from the sheet.
(3) The transfer sheet of the above (1), wherein the sheet contains two or more holding areas.
(4) The transfer sheet of the above (3) wherein the holding areas hold different biologically active substances or different combinations of two or more biologically active substances.
(5) The transfer sheet according to the above (3), wherein the holding areas hold a biologically active substance in different concentrations.
(6) The transfer sheet according to the above (1), wherein the sheet base is made from an elastic or flexible film at least at the holding area.
(7) The transfer sheet according to the above (1), wherein the holding area is a protruding portion provided on the sheet base, and the biologically active substance is held on the protruding area.
(8) The transfer sheet according to the above (1), wherein a holding layer is formed on an entire or partial surface of the sheet base for holding a biologically active substance thereon.
(9) The transfer sheet according to the above (1), wherein the holding area is able to release the biologically active substance in a sustainable manner or the area releases a biologically active substance provided with a property for sustained release.
(10) The transfer sheet according to (1), wherein each holding area or a group of two or more areas is surrounded by a protruding wall structure.
(11) A method for producing a transfer sheet according to any of (1) to (10), the method comprising a step of providing a holding area with a biologically active substance by using liquid discharge means.
(12) The method according to (11), wherein the liquid discharge means is discharge means by a thermal ink jet method.
(13) The method according to (11), wherein the liquid discharge means is discharge means by a piezo ink jet method.
(14) The method according to any of (11)-(13), further comprising a step of immobilizing the biologically active substance by applying an immobilizing energy from the exterior.
(15) A method for screening cell culture conditions utilizing a transfer sheet of any of (1) to (9), the method comprising the steps of placing the transfer sheet on a plate having at least one culture region to cover the culture region containing a culture liquid with a holding area holding a biologically active substance on the transfer sheet; and supplying the culture liquid with the biologically active substance from the holding area.
(16) The screening method according to (15), further comprising a step of replenishing the culture liquid with a substance necessary for screening.
(17) The screening method according to (15) or (16), further comprising a step of replacing the sheet with another transfer sheet of a same or different type.
(18) The screening method according to any of (15)-(17), further comprising a step of observing a morphological change of the cell.
(19) The screening method according to (18), wherein cells are stained for evaluation.
(20) The screening method according to any of (15)-(19), further comprising a step of executing a quantitative determination of a substance synthesized in the cell.
(21) The screening method according to any of (15)-(19), further comprising a step of executing a quantitative determination of a substance incorporated in the cell.
(22) The screening method according to (20) or (21), wherein the step of executing a quantitative determination is carried out by at least one of a radiation intensity measurement, a fluorescence intensity measurement, a luminescence intensity measurement and an optical absorbance measurement.

The present invention also provides a cell culture kit including the following embodiments. Such a cell culture kit comprises a culture plate having at least one culture region for culturing a cell; and a sheet having a portion to cover the culture region; wherein each of the culture region and the covering portion holds at least one substance having a biological activity to a cell, and at least one biologically active substance held by the culture region or the covering portion is immobilized thereon.

The kit may contain two or more combinations of the culture regions and the covering portions.

The cell culture kit may have a constitution wherein the biologically active substance held in the culture region is immobilized thereto, the biologically active substance held in the covering portion is attached so as to be released in contact with a culture liquid, and the sheet base and the covering portion constitute a transfer sheet for transferring the biologically active substance to the culture region.

The present invention also provides a method for producing a cell culture kit of the aforementioned configuration characterized in that at least liquid discharge means is utilized for providing the culture region and the covering portion with the biologically active substance. The liquid discharge means is of a thermal ink jet method, or of a piezo ink jet method.

The present invention also provides a screening method utilizing a cell culture kit of the aforementioned configuration, where the method comprises the steps of placing a sheet having a covering portion on a plate having a culture region to cover the culture region with the covering portion, culturing a cell in the culture region covered with the covering portion in contact with a first biologically active substance immobilized one of the culture region and the covering portion; and supplying the culture liquid with a second biologically active substance attached to the rest of the culture region and covering portion. The cell culture kit of the invention allows secure disposition of a biologically active substance to a desired position by a simple process, and can be utilized for screening (evaluating) the effects of various biologically active substances for the cells.

More specifically, screening with the cell culture kit of the invention allows to specify a factor necessary for proliferation, differentiation, survival, maintenance of undifferentiated state, death or substance production, whereby an efficient cell culture method can be determined. Also according to the present invention, substances can be screened not only in their solid phase but also in their liquid phase, that is, screening is carried out under conditions closer to in vivo conditions using combinations of biologically active substances in their immobilized state or dissolved state. The present invention also allows investigation of difference in the effect of a substance in its solid phase and in its liquid phase or combination thereof, and evaluation of individual sensitivity to a drug or an endocrine perturbing substance, so-called environmental hormone. It is also possible, based on the result of such evaluation, to determine a tailor-made therapeutic method for individuals. It is furthermore possible to screen useful substances having biological activities to cells using cells.

The transfer sheet and the cell culture substrate of the invention can be produced employing an ink jet method as the liquid discharge means, enabling simultaneous action of plural substances on the cells at various concentrations by choosing liquid species and controlling a number of liquid droplets. Also the transfer sheet of the invention allows precise transfer of plural substances in a cell culture liquid, enabling exact evaluation of an effect of a system comprised of plural biologically active substances to the cell proliferation, differentiation and survival, which has been difficult to evaluate in the prior technology. Also a successive addition of biologically active substances or change in combination is easy. Therefore, the effect of such conditions can be studied easily and effectively. Furthermore, the cell culture substrate of the invention can be easily produced in a large scale, and stored stably and used whenever desired as a screening substrate.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the description, illustrate embodiments of the invention and, together with the description, serve to explain the principles of the invention.

BEST MODE FOR CARRYING OUT THE INVENTION

Preferred embodiments of the present invention will now be described in detail in accordance with the accompanying drawings.

Figure 1A:
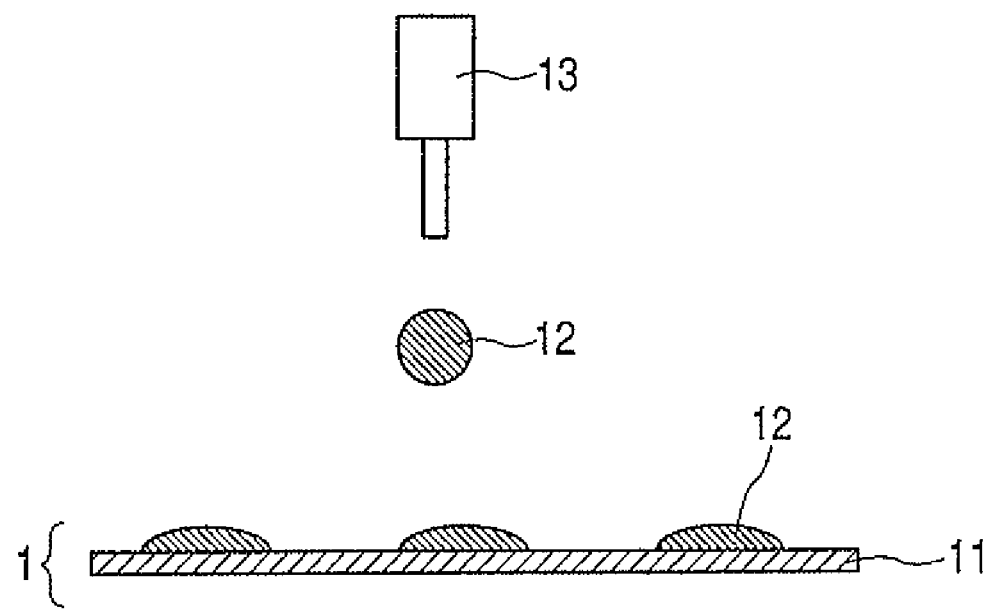
FIGS. 1A and 1B illustrate an example of a producing method of a biologically active substance transfer sheet of the present invention.
Figure 2:
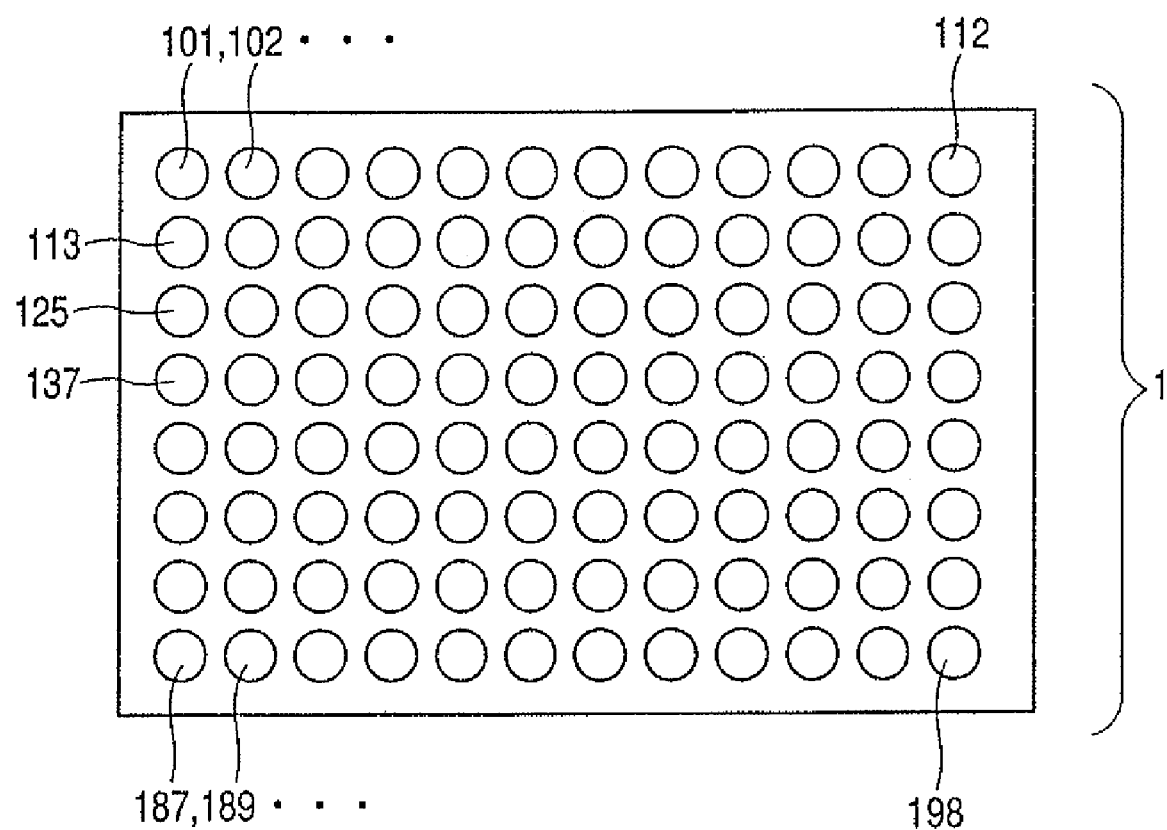
FIG. 2 illustrates an example of biologically active substance forming areas in a biologically active substance transfer sheet.

First, there will be explained an example of a biologically active substance transfer sheet (transfer sheet) of the invention. As shown in FIG. 1A, the transfer sheet 1 is constituted of a base (substrate) 11 and two or more biologically active substances 12 which are positioned in desired positions of the base 11 with different densities or concentrations forming a pattern. FIG. 2 shows a transfer sheet 1 on which two or more biologically active substances 12 are patterned in 96 areas (101-196). Thus, when two or more active substances 12 provided in one area of the pattern come into contact with the culture liquid in a region corresponding that area, the active substances are liberated and dissolved in the culture liquid, in which the cells are cultured. Accordingly, after the culture, one can observe difference in at least one of cell adhesion, proliferation, differentiation, survival, maintenance of the undifferentiated state, death, and substance production induced by various combinations of the biologically active substances 12. One of the advantages obtained by preparing the transfer sheet with the liquid discharge means is that the biologically active substances can be easily positioned in a patterned area with an arbitrary ratio.

A cell employable in the present invention may be any procaryotic or eucaryotic cells. For example, there can be employed a bacteria cell, an yeast cell, a protozoa cell, a neuron, a fibroblast, a smooth muscle cell, a skeletal muscle cell, a gliocyte, an embryonic stem cell, a hematopoietic stem cell, a mast cell, a fat cell, a nerve stem cell or an immune cell including T cell and B cell, or a cluster thereof including transformed or non-transformed cells.

The biologically active substance 12 is a substance that affects cellular functions such as adhesion property, proliferation, differentiation, survival, maintenance of undifferentiated state, death (apoptosis), substance production, gene expression and cellular signal transmission. Examples of such substance include an extracellular matrix protein, an antibody having a specific binding ability to the cell surface, a cytokine, and a chemical substance that affects cell proliferation or differentiation when taken into the cells. Examples of the extracellular matrix protein include collagen, fibronectin and laminin. Cytokine includes a cell growth factor and a hormone, and the cell growth factor includes a nerve growth factor (NGF), an epithelium growth factor (EGF), a basic fibroblast growth factor (bFGF), a bone morphogenetic protein (BMP-2), an insulin-like growth factor (IGF-I), and a tumor necrosis factor (TNF). Also examples of hormone include a peptide such as insulin or calcitonin, a steroid such as aldosterone or progesterone, and an amino acid derivative such as epinephrine or thyroxine. There are also included other chemical substances such as allergen which induces allergy, and so-called endocrine-perturbing substances. There are further included antibiotics which can suppress bacterial growth. There are further included an antibody that specifically binds to the aforementioned substance thereby allowing to investigate localization of such a substance in the cell, and a neutralizing antibody capable of suppressing the function of such substance. On the base 11, various combinations of plural different biologically active substances can be provided in different areas. On the base 11, there may be formed, not only areas which are different in the combination of plural different biologically active substances, but also areas in which the density of the biologically active substance 12 differs.

Figure 3:
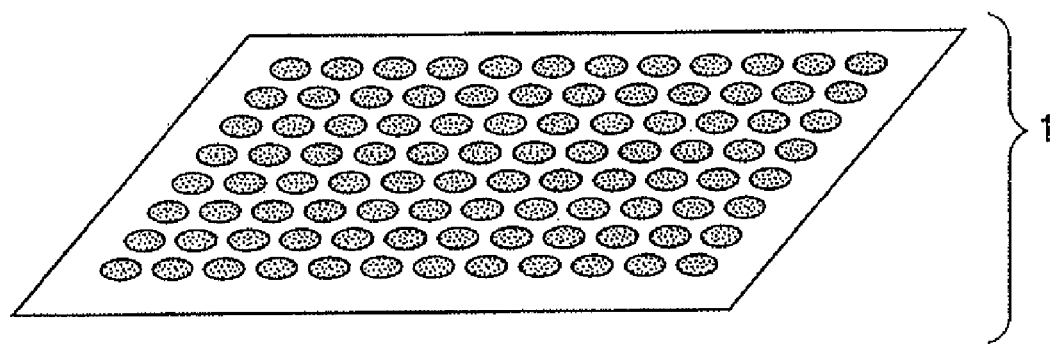
FIG. 3 illustrates an example of attaching a biologically active substance transfer sheet to a 96-well transparent microplate to transfer the biologically active substance to the culture medium.
Figure 3:
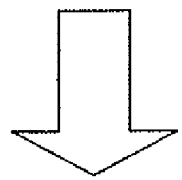
Figure 3:
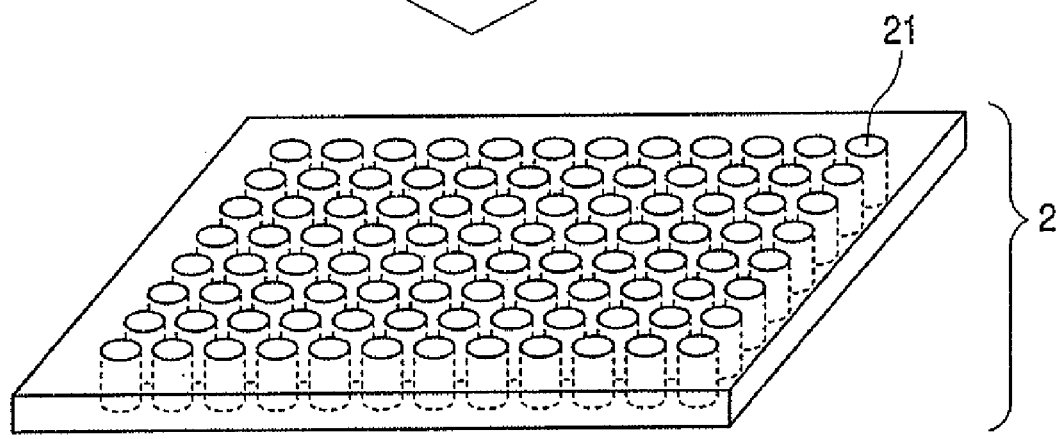
Figure 4:
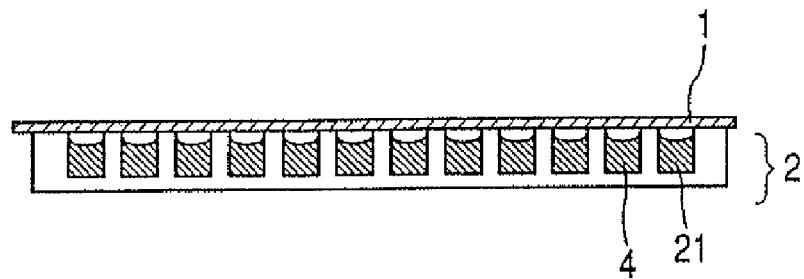
FIG. 4 is a cross-sectional view of a state where a biologically active substance transfer sheet is attached to a 96-well transparent microplate.

When such areas come into contact with a culture liquid in the regions corresponding to the areas, the active substance 12 is liberated and dissolved in the culture liquid, in which cells are cultured. FIG. 3 shows an example. The transfer sheet 1 having the pattern of the aforementioned 96 areas covers a microplate 2 (96-well) containing a cell culture liquid in each well, in such a manner that each of the 96 areas of the transfer sheet 1 covers the corresponding well 21. FIG. 4 is a schematic cross-sectional view of a mutually adhered state.

Then the sheet 1 and the microplate 2 in a superposed state are vibrated or rotated to liberate and dissolve the active substance held on the sheet 1, into the cell culture liquid. Then, after sheet 1 is removed from the microplate, a cell suspension is added to each well to culture the cells. After the culture, one can observe in detail any difference in cell adhesion, proliferation, differentiation, survival, maintenance of an undifferentiated state, cell death, or substance production according to combinations of the active substances 12 or densities thereof. In the above example, the contact was carried out immediately before the start of culture. However, in the invention, the transfer sheet may be brought into contact with the culture liquid 4 at an arbitrary timing after the start of the cell culture as shown in FIG. 4, to liberate and dissolve the active substance into the culture liquid.

Figure 5:
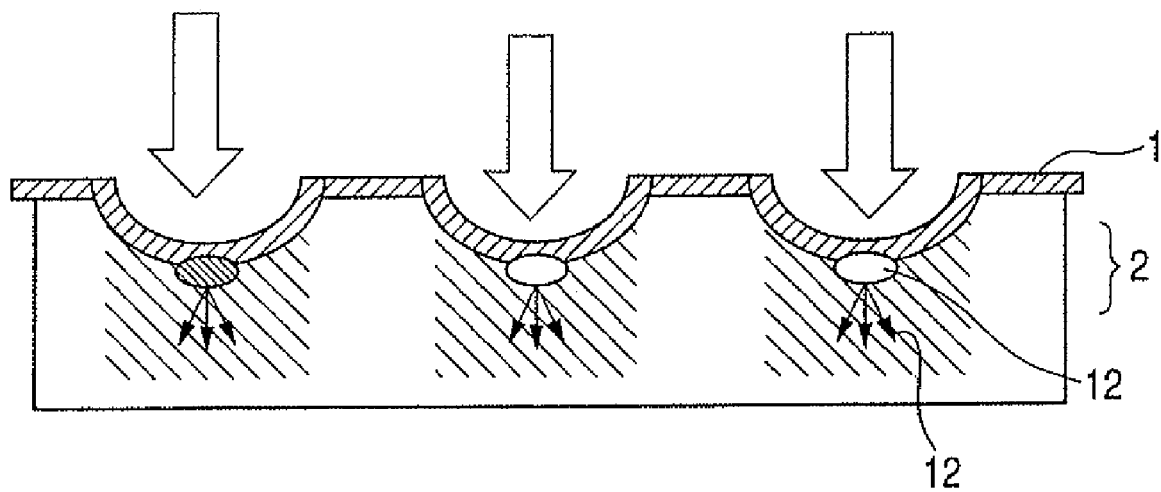
FIG. 5 illustrates an example of transfer of a biologically active substance from a biologically active substance transfer sheet to a transparent microplate.

The base 11 can be made of any material of any shape, as long as it can hold the active substance. More specifically, a glass plate, a plastic plate, a plastic sheet, a polymer film or a paper can be employed advantageously. Also the base 11 may be transparent, opaque, or colored. Also the base 11 may be formed by a stretchable, elastic or flexible film. In such a case, synthetic rubber such as silicone rubber, natural rubber or a paraffin film can be advantageously employed. When the areas holding the active substance on the transfer sheet are brought into close contact with the cell culture wells for achieving the contact with the culture liquid therein and for liberating and dissolving the active substance therein, a stretchable or elastic sheet is preferable as it provides satisfactory adhesion to prevent leakage of the liquid. Also it is possible to press down the stretching or flexible transfer sheet, using a pointed article from the above until the sheet comes in contact with the surface of the culture liquid 4, thereby dissolving the active substance into the culture liquid as shown in FIG. 5. In this case, there is obtained an advantage that the biologically active substance can be liberated and dissolved without rotation or shaking.

Also in the base 11, each area in which the active substance 12 is positioned, or a group of two or more areas, may be in a recess. Such a configuration facilitates positioning of liquid droplets by liquid discharge means. A base having such recess can by formed by a molding of a resinous material or an etching method utilizing a photolithographic technology.

Figure 1B:
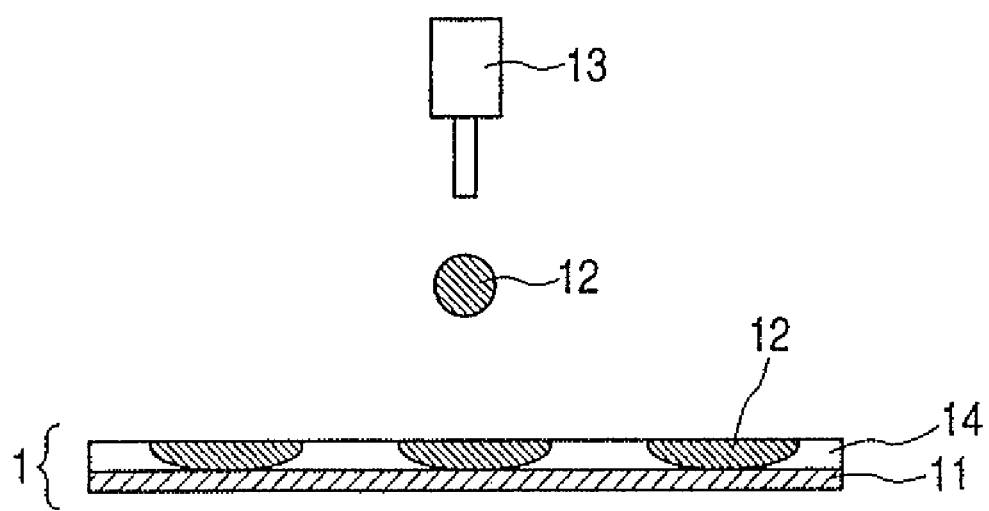

Also in the base 11, each area in which a biologically active substance 12 is positioned, or a group of two or more areas, may be surrounded by a wall structures. Such configuration can facilitate positioning of liquid droplets by liquid discharge means. A base having such wall-shaped structure can by formed for example by photolithography. Alternatively, the base 11 may have protruding portions, and the active substance 12 may be provided on such protruding portions. In such a case, the active substance 12 can be easily dissolved in the culture liquid 4 by merely inserting the protruding portion into a culture well. Such protruding shape can be prepared by press molding with a metal mold. Also an adhesive material, or a water repellent material may be applied or printed in an area where the active substance is not positioned. Also, as shown in FIG. 1B, a holding layer 14 which holds the biologically active substance may be formed on an entire or partial surface of the base 11.

The holding layer 14 is to help prompt release and dissolution of the biologically active substance on contact with the culture liquid in the culture well. Therefore the holding layer 14 is preferably made of a water-soluble or water swelling substance, which preferably can hold the biologically active substance stably. Preferable examples include a synthetic polymer such as polyvinyl alcohol, polyethylene glycol, a polyacrylic acid salt, a polymethacrylic acid salt, a methacrylic acid copolymer, methyl cellulose, ethyl cellulose, hydroxypropyl cellulose, hydroxypropylmethyl cellulose, hydroxypropylmethyl cellulose phthalate, cellulose acetate phthalate, carmerose, or polyvinylpyrrolidone, a starch derivative such as starch, hydroxyethyl cellulose, sodium alginate, sodium celluloseglycollate, or sodium starchglycollate, a natural polymer such as dextrin, gum Arabic, carrageenan, agar, gelatin, tragacanth or crystalline cellulose, or a water-soluble compound such as glucose, sucrose, fructose, or xylitol. Such a material may be applied on an entire or partial surface of the base 11 as required. The holding layer 14 can be coated, for example, by using bar coating, blade coating, screen printing, flexographic printing or offset printing. The thickness of the holding layer can be arbitrarily selected, but is preferably about 1 to 100 μm.

By suitably selecting the configuration of the holding layer, it is possible to attain sustained release of the biologically active substance from the holding layer into a culture liquid. Such sustained or controlled release may also be achieved by adding, a substance enabling controlled release such as a water-soluble styrene-acrylic resin to a liquid containing the biologically active substance, which liquid is used at application of the biologically active substance to the sheet.

Such a transfer sheet 1 can be prepared in the following manner (cf. FIGS. 1A and 1B). First, a base 11 may be subjected to a pretreatment mentioned above if necessary. More specifically, the base 11 is washed to eliminate undesired materials and may be subjected to various chemical or physical treatments such as UV irradiation or corona discharge.

The biologically active substance 12 is deposited either directly on such base 11, or on a sheet prepared by forming a holding layer 14 on an entire or partial surface of the base 11. Liquid discharge means 13 is employed for depositing. The liquid discharge means 13 is capable of discharging a liquid droplet of a volume of 100 nl or less per drop, more specifically 1 nl or less, such as a micropipette, a microdispenser, or a discharge apparatus of ink jet method. A discharge apparatus of ink jet method can be employed particularly advantageously because the discharge apparatus is available inexpensively and a minute liquid droplet can be discharged. Furthermore, among the ink jet methods, a thermal ink jet method and a piezo ink jet method can be employed advantageously. A discharge apparatus of the thermal ink jet method, being easy in preparation of fine discharge ports, can discharge a liquid containing a biologically active substance 12 in predetermined positions at a high density. Also a discharge apparatus of the piezo ink jet method, in which a discharge energy is generated by a displacement of a piezoelectric element, can discharge the biologically active substance 12 without giving a thermal stress thereto.

The biologically active substance 12 is dissolved or dispersed in an appropriate solvent for discharge. Any solvent (dispersion medium) may be employed as long as it can stably dissolve or disperse the biologically active substance 12, but water is employed advantageously. Water content is 30 mass % or higher, preferably 50 mass % or higher. Preferably, water is ion-exchanged water (deionized water) or various buffers for stably dissolving the biologically active substance 12. Also, if necessary, a water-soluble solvent may be employed. The amount of each water-soluble solvent to be added is 50 mass % or less, preferably 30 mass % or less. Any water-soluble solvent may be employed as long as it is soluble in water, and examples include an alkyl alcohol with 1 to 4 carbon atoms such as methyl alcohol, ethyl alcohol, n-propyl alcohol, isopropyl alcohol, n-butyl alcohol, sec-butyl alcohol, or t-butyl alcohol; an amide such as dimethylformamide or dimethylacetamide; a ketone or a ketoalcohol such as acetone or diacetone alcohol; an ether such as tetrahydrofuran or dioxane; an polyalkylene glycol such as polyethylene glycol, or polypropylene glycol; an alkylene glycol in which an alkylene group has 2-6 carbon atoms such as ethylene glycol, propylene glycol, butylenes glycol, triethylene glycol, 1,2,6-hexanetriol, thiodiglycol, hexylene glycol or diethylene glycol; glycerin; a lower alkyl ether of a polyhydric alcohol such as ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, or triethylene glycol monobutyl ether; N-methyl-2-pyrrolidone, 2-pyrrolidone and 1,3-dimethyl-2-imidazoline. These solvents may be suitably selected in one or more kinds. Among these water-soluble organic solvents, there is preferred a polyhydric alcohol such as diethylene glycol, or a lower alkyl ether such as triethylene glycol monomethyl ether. In case of thermal ink jet method, addition of an alcohol such as ethanol or isopropyl alcohol or a lower alkyl ether of a polyhydric alcohol is advantageous for more stable bubble formation on a thin film resistor in a discharge port of the ink jet head for providing the biologically active substance.

The solution of the biologically active substance 12 may further include, if necessary for obtaining desired physical properties, a surfactant, an anti-foaming agent, an antiseptic, an inorganic salt, an organic salt and the like.

As to the surfactant, any surfactant not detrimentally influencing the biologically active substance 12 for example on a storage stability may be employed, for example an anionic surfactant such as a fatty acid salt, a higher alcohol sulfate ester salt, a liquid fatty oil sulfonate ester salt, or an alkylalylsulfonic acid salt, or a nonionic surfactant such as an polyoxyethylene alkyl ether, a polyoxyethylene alkyl ester, a polyoxyethyelensorbitan alkyl ester, acetylene alcohol or acetylene glycol, and these may be employed singly or in a mixture of two or more kinds.

In order to release the biologically active substance 12 gradually from the transfer sheet, a hydrophilic polymer compound may be added to the solution in addition to the foregoing components. For example, polyvinyl alcohol, a polyacrylic acid salt, a polymethacrylic acid salt, a methacrylic acid polymer, methyl cellulose, ethyl cellulose, hydroxypropyl cellulose, hydroxypropylmethyl cellulose, hydroxypropylmethyl cellulose phthalate, cellulose acetate phthalate, or polyvinylpyrrolidone is advantageously employed for providing the controlled release property. Such hydrophilic resin is preferably added within a range of 1 to 10 mass %, more preferably 2 to 5 mass %.

After the biologically active substance 12 is provided in a desired position on the base 11 by the liquid discharge means 13, the sheet may be dried, for example, in an oven.

The transfer sheet can be prepared as explained above.

The transfer sheet can be stored in a container over a prolonged period. A more preferable stable storage can be achieved by sealing the transfer sheet in a container together with a drying agent or an oxygen removing agent.

In the following, there will be explained a screening process utilizing the aforementioned transfer sheet.

The process comprises the following steps of: contacting each area carrying the biologically active substance of the transfer sheet with the culture liquid in a corresponding culture well thereby transferring the biologically active substance to the culture liquid; and culturing cells therein.

This method enables an easy transfer of the biologically active substance at the same time to plural culture regions (wells) of a cell culture vessel or plate. It is also possible to transfer the biologically active substance(s) plural times during the culture period by contacting plural transfer sheets of the same or different kind to the culture liquid. The culture liquid may be changed when the transfer sheet is replaced to remove the previously added biologically active substance. In such a case, it is possible to supply the same biologically active substance to the same culture region by using a transfer sheet of the same biologically active substance, or to supply a different biologically active substance to change the culture conditions by using a transfer sheet carrying a different biologically active material. Such a change may be carried out at any number of times according to the necessity. Thus it is possible to investigate the influence of one or more biologically active substances to the cell in detail and in a time-series manner. Also use of the transfer sheet of the invention is simple and avoids contamination with undesired substances.

As the culture vessel, a commercially available microplate can be advantageously employed. The microplate contains an array of a plurality of culture regions called wells. The number of wells can be about 12 to 2,000, and can be suitably selected according to the number of the biologically active substances to be screened and conditions thereof. For example a commercial 96-well microplate can be advantageously employed in case of screening up to 96 conditions by using a cell culture.

In the transfer sheet of the invention, areas carrying the biologically active substance are patterned corresponding to the positions of wells of the microplate in such a manner that each area comes just above the corresponding well when the sheet is superposed on the microplate. As shown in FIG. 2, the transfer sheet is placed so as to cover the microplate, and the biologically active substance is dissolved/extracted with the liquid put in the well in advance. In this manner, the biologically active substance is transferred from the transfer sheet into each well of the microplate.

Cells are cultured in such a culture vessel under the influence of the biologically active substance(s) on cellular functions such as cell adhesion, proliferation, differentiation, survival, maintenance of an undifferentiated state, death of cells, or substance production. The cells to be used are not particularly restricted, and any cells may be employed for this purpose. Also one kind or two or more kinds of cells can be used at a time for screening. Prior to the cell culture, the transfer sheet and the cell culture vessel may be sterilized if necessary for example by ultraviolet irradiation or by washing with alcohol. Such an operation may prevent contamination of the culture, for example, with undesired microorganisms.

Alternatively, a desired substance may be added to the culture liquid of a desired region of the culture vessel 2 during the cell culture or after the cell culture for a predetermined period, by using the transfer sheet. In this manner it is possible to change proliferation, differentiation, survival, maintenance of an undifferentiated state, death, or substance production of the cells or change an adhesion property thereof to the substrate. Also after the cell culture, a desired substance such as an indicator may be added in a desired area. In this manner the screening can be carried out easily.

Also the cultured cells may be removed from the culture vessel during the cell culture therein or after cultured for a predetermined period. In this manner the removed cultured cells may be utilized as an artificially prepared tissue or a part thereof. More specifically, the cultured cells can be removed by treating the cell culture vessel with trypsin after the cell culture. Also by coating the cell culture vessel in advance with a polymer of which hydrophilicity changes with temperature, such as poly(N-isopropylacrylamide), and executing the cell culture thereon, it is possible to remove the cultured cells by bringing the temperature to about 30° C., thereby changing the hydrophilicity of the polymer surface. In this manner the cells can be utilized for example for a live tissue.

Next, screening means for cells cultured in the aforementioned cell culturing vessel is explained.

As screening means, morphological changes of the cells cultured in the cell culture vessel 2 can be observed. For this purpose, any microscope capable of observing the shape of the cells can be used such as an optical microscope a scanning electron microscope, a transmission electron microscope, a scanning probe microscope and a fluorescence microscope. A cell culture plate bearing cultured cells is placed under such a microscope to observe the morphology of the cells. Screening or evaluation can be simply carried out by mere microscopic observation of the cells. Also the cells may be stained for evaluation. Cell staining facilitates evaluation under a microscope when cells have proliferated to a high density or fused by differentiation forming polykaryocytes.

In addition to the morphological observation, one can quantitatively determine a substance produced or incorporated by the cells while the cells adhered to the culture vessel wall and proliferated or differentiated thereon. In case an object substance cannot be directly determined, the quantitative determination may be carried out with an alternative substance. For example, an object protein can be quantitatively determined by introducing a gene of a measurable protein in the vicinity of the gene of the object protein by the genetic engineering, and by quantitatively determining the measurable protein. Thus cellular changes induced by the substance immobilized on the base of the culture vessel can be studied in detail by measuring such a product, which leads to clarification of the information transmission mechanism in the cell. When a substance incorporated into the cell is evaluated, the substance to be taken into the cells can be labeled in advance, which makes the quantitative determination rather easy.

For a quantitative determination of these substances, there may be employed a method of measuring radiation from a radioactive compound, a method of measuring an amount of fluorescence emitted from a substance labeled with a fluorescent substance, a method of measuring an amount of light emitted from a light-emitting substance, or a method of measuring an optical absorbance of a dye.

A method that employs a radioactive compound containing a radioactive isotope of an element abundantly present in a live tissue such as hydrogen, carbon, nitrogen, phosphor or sulfur and measures the intensity of radiation from such a compound is highly sensitive, and allows observation of phenomena occurring in a live body, because such a hot compound has the same chemical properties as the cold compound.

Also a method of labeling with a fluorescent substance is relatively simple and gives little influence on the metabolism of the cell by employing a fluorescent substance of a low molecular weight. Also in a quantitative determination of a substance produced by the cells by a determination method utilizing an antigen-antibody reaction, an evaluation by a fluorescent measurement is effective since various antibodies labeled with a fluorescent substance are available and provide a high measuring sensitivity.

Also the method of measuring luminescence from a luminescent substance allows to recognize even a small change, since the luminescence can be measured with a high sensitivity. When a gene expressed with cell adhesion, proliferation, differentiation or substance production caused by a substance has been specified, it is possible to introduce a firebug luciferase gene or the like in the vicinity of such a gene and an amount of luciferase produced by the gene expression is measured from the intensity of luminescence generated on addition of ATP and luciferin. In this manner it is possible to evaluate the influence of the screened substances from the luminescence intensity.

In a method of measuring the optical absorbance of a dye, it is possible to amplify the optical absorbance of a dye for example by employing an enzyme reaction in combination, thereby enabling a quantitative determination of a substance of a very small amount.

(Embodiment of Cell Culture Kit)

A cell culture kit of the present embodiment is constituted at least of a cell culture plate having plural divided culture regions (sections), and a sheet having covering portions for covering the culture regions. In either of the culture region and the corresponding covering portion, at least one biologically active substance having a biological activity on a cell is immobilized, and, on the rest, at least one biologically active substance is held in a manner releasable to a culture liquid. Thus, the biologically active substance may be immobilized on the culture plate or to the sheet. When the active substance is immobilized on the plate, another biologically active substance on the sheet is held to be releasable to the culture liquid. When the active substance is immobilized on the sheet, another biologically active substance on the culture plate is held in a releasable state to the culture liquid.

In the following, the present invention will be explained by a configuration in which the biologically active substance on the sheet is held releasably to the culture liquid to constitute a transfer sheet, but the present invention is not limited thereto. A biologically active substance may be immobilized on the he sheet.

When a biologically active substance is immobilized to the culture plate, the kit is constituted of a cell culture plate on which one or more biologically active substances are immobilized in desired areas, and a transfer sheet on which one or more biologically active substances are arranged in plural areas.

In the cell culture plate, a combination of biologically active substances immobilized in one region may be different between the regions. Also a density of a biologically active substance immobilized may be different between the regions of the cell culture plate. Furthermore, a region of the cell culture plate may immobilize plural biologically active substances, thereby constituting plural regions of different screening functions. Also a group of two or more regions may be provided in a recess, or a group of two or more regions may be surrounded by a protruding wall-shaped structure.

In the transfer sheet, it is preferable that plural biologically active substances are releasable from the sheet. The transfer sheet may contain, in the plural areas thereof, plural areas different in the combination of the biologically active substances. The transfer sheet may contain, in the plural areas thereof, plural areas different in a density of the biologically active substance. The sheet base may be constituted of a stretchable or flexible sheet at least in an area holding the biologically active substance. In the transfer sheet, a holding layer for carrying the biologically active substance may be formed on an entire or partial surface of the sheet base. Also in the transfer sheet, each area may be formed in a recess. Also in the transfer sheet, each area may be formed on a protruding portion formed on the sheet. Also in the transfer sheet, each area or a group of two or more areas may be surrounded by a protruding wall-shaped structure.

The cell culture plate and the transfer sheet can be prepared by a method including a step of positioning each biologically active substance by liquid discharge means in plural regions of the cell culture plate or in plural areas in each region, and/or in plural areas on the releasable transfer sheet. To produce the cell culture plate and the transfer sheet, the thermal ink jet method or the piezo ink jet method can be employed as the liquid droplet discharge means. Also an energy for immobilizing the biologically active substance to the cell culture plate may be applied from the exterior.

A screening method utilizing the transfer sheet includes steps of culturing cells in a culture liquid in contact with a region immobilizing a biologically active substance of the cell culture plate, contacting the culture liquid with an area holding a biologically active substance of the transfer sheet thereby releasing and dissolving the biologically active substance into the culture liquid in which the cells are cultured. The screening method may include a step of replenishing a substance necessary for the screening, by utilizing plural transfer sheets. In such a case, it is possible to supply the same biologically active substance to the same culture region by replacing with the same transfer sheet during the culture, or to change the culture conditions by changing the sheet to a different sheet to add a different biologically active substance. Such change may be any number of times according to the necessity. Also there may be included a step of executing a culture under a gradual supply of the biologically active substance to the cells in the culture liquid, by employing a transfer sheet in which a biologically active substance is provided on a holding layer that enables sustained release and contacting such a sheet with the culture liquid during an entire culture period or a part thereof.

Screening in the screening method of the present embodiment can be carried out, for example, based on at least one of following items:

(1) A change in cell morphology is evaluated in a desired area of the plate.

(2) A substance incorporated in the cells is quantitatively determined in a desired area of the plate.

(3) A substance synthesized in the cells is quantitatively determined in a desired area of the plate.

(4) A shape evaluation or a quantitative determination of a substance is carried out by cell staining.

(5) A signal by a reporter gene is detected.

(6) An evaluation is carried out by a site blot assay.

(7) A quantitative determination of a substance is carried out by a measurement of a radiation intensity.

(8) A quantitative determination of a substance is carried out by a measurement of a fluorescent intensity.

(9) A quantitative determination of a substance is carried out by a measurement of a luminescent intensity.

(10) A quantitative determination of a substance is carried out by a measurement of an optical absorbance.

The embodiments will be explained in the following in more detail.

Figure 6A:
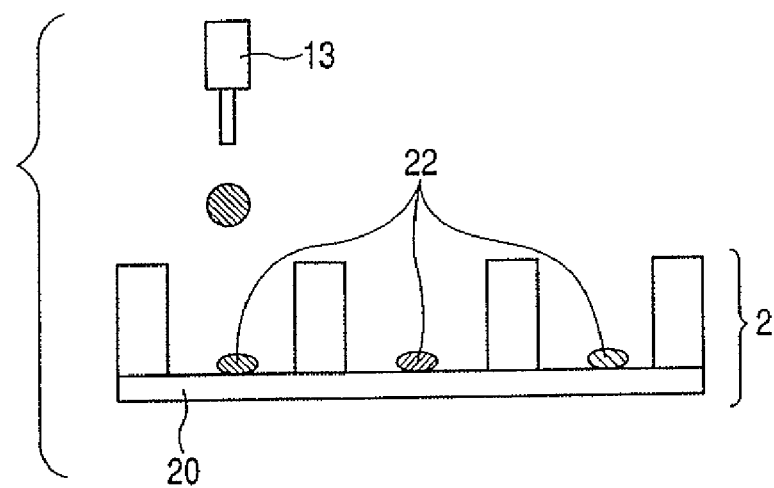
FIGS. 6A, 6B and 6C illustrate an example of a method for producing a cell culture kit by using liquid discharge means.
Figure 6B:
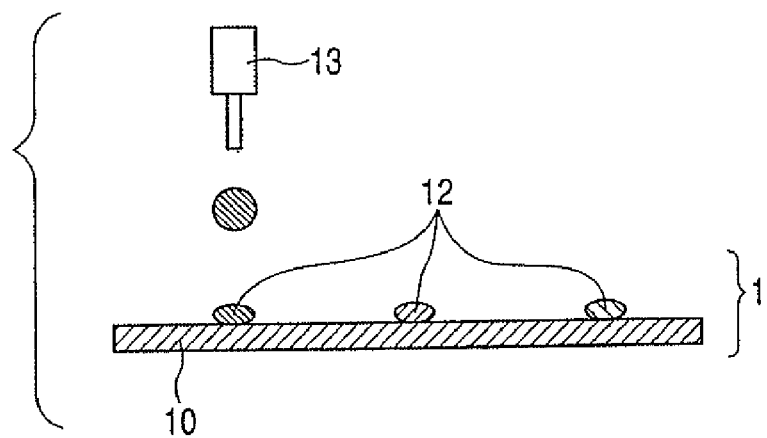
Figure 6C:
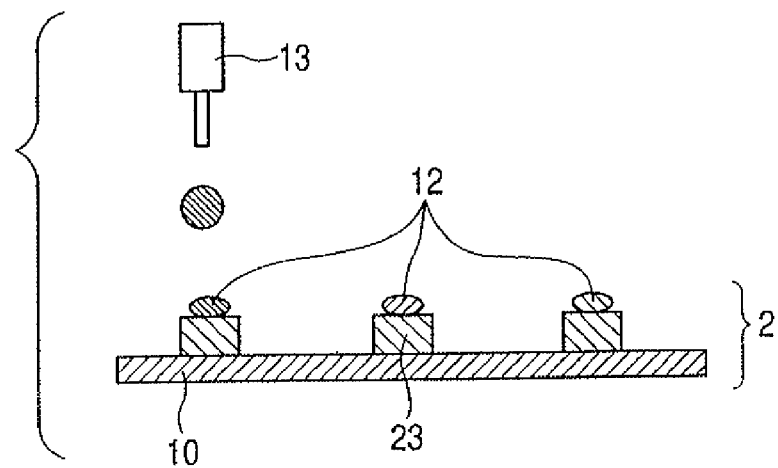
Figure 7A:
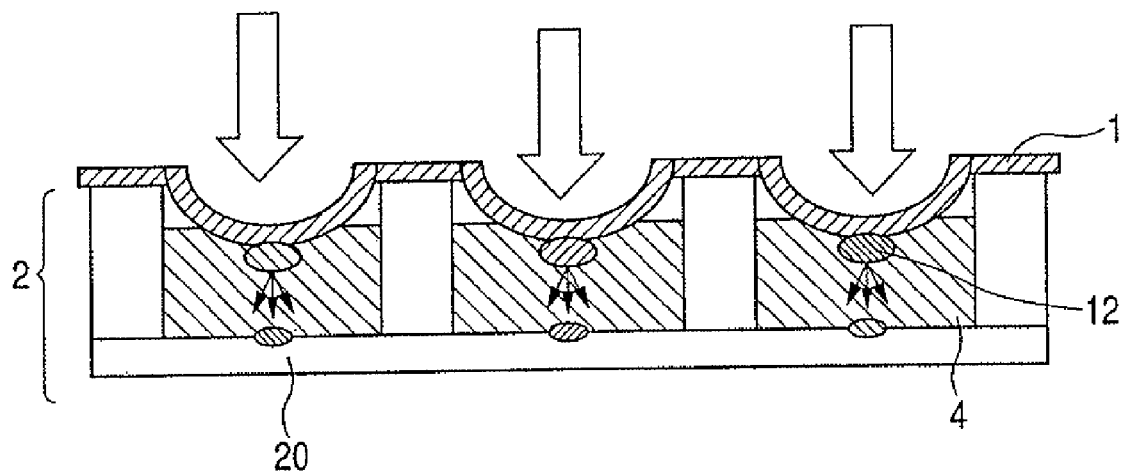
FIGS. 7A and 7B illustrate an example of a cell culture process utilizing a cell culture kit.
Figure 7B:
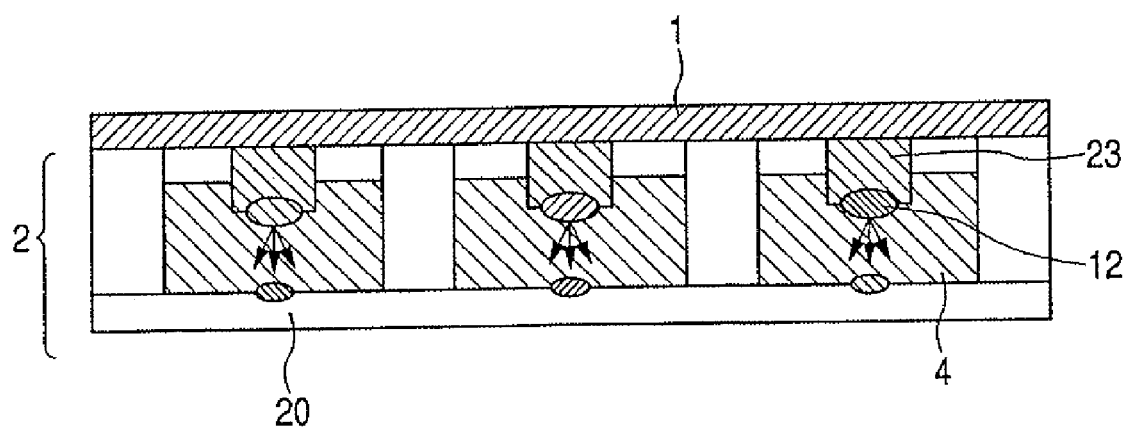

In the following there will be explained an example of the cell culture kit of the present invention. As shown in FIG. 6A, in a cell culture plate 2, one or more biologically active substances 22 (3 kinds in FIG. 6A) are provided in desired regions formed on a base (substrate) 20, and each biologically active substance 22 is immobilized on the base 20. On the other hand, in a transfer sheet 1, two or more biologically active substances 12 are provided on a sheet shown in FIG. 6B, at desired positions corresponding to the regions of the cell culture plate. It is also possible, as shown in FIG. 6C, to provide the biologically active substance 12 on a protruding portion 23 formed on the sheet. For positioning, liquid droplet discharge means 13 can be utilized. In culturing the cells with the cell culture plate 2, prior to the start of the culture or at an arbitrary timing after the start of the culture, the transfer sheet is placed so as to cover the cell culture plate 2 as shown in FIG. 7A, and the sheet is depressed from the above to achieve a contact with the culture liquid 4 and the sheet, thereby releasing and dissolving the biologically active substance in the culture liquid, whereby the biologically active substance 22 immobilized on the cell culture plate and the biologically active substance 12 provided on the transfer sheet act on the cells and there can be inspected a higher-order effect of a combination of the biologically active substances (12, 22) in the immobilized and dissolved states. Also in case of employing a sheet in which the biologically active substance 12 is provided on the protruding portion 23 formed on the sheet (FIG. 6C), it is possible to contact the area of the biologically active substance with the culture liquid 4 to induce liberation and dissolution by merely placing the sheet 1 to cover the cell culture plate 2 (FIG. 7B).

A cell employable in the present embodiment may be any procaryotic or eucaryotic cell, and such cells may be suitably selected.

In the present embodiment, the biologically active substances 22, 12 can be the aforementioned substances for culture control, and such substance may be arbitrarily immobilized to the base 20 or positioned on the sheet 10 in consideration of the action to the cells or localization in the cells.

Also as to the biologically active substance 22 and/or the biologically active substance 12, a combination of the biologically active substances 22 and 12 may be different depending on an area/region or on a group of two or more areas/regions of the base 20 and the sheet 10. It is thus possible to evaluate at least a difference in the effects in the combination of the biologically active substances 22 and 12 to the cells.

Also the biologically active substances 22 and 12 may be different in density according to the position on the base 20 and the sheet 10. In this manner it is possible to evaluate in more detail difference of the biological activity on the cells due to the density of the biologically active substance 22 and/or a difference in the concentration of the biologically active substance 12 in the culture liquid.

One of the advantages obtained by the use of the liquid discharge means is that the biologically active substance can be easily positioned in an area with an arbitrary amount.

The immobilization of the biologically active substance 22 on the base 20 may be achieved by a covalence bond, an electrostatic attractive force or a biological affinity. Immobilization by a covalence bond to the base 20 allows strong immobilization of the biologically active substance 22, of which bonding is scarcely affected by the cells or by the culture liquid, whereby a stable immobilization on the base 20 can be attained.

The base 20 and the sheet 10 can be made of any material of any shape, as long as the biologically active substance can be stably immobilized or held. More specifically, a glass plate, a plastic plate, a plastic sheets a polymer film or a paper can be employed advantageously. Also the base 20 and the sheet 10 may be transparent, opaque, or colored. Also for immobilizing the biologically active substance 22 on the base 20 or for improving stability of the biologically active substances 22, 12 on the base 20 and the sheet 10, a treatment with a chemical material or irradiation may be applied on the entire surface or a part thereof. Also an adhesive material, or a water repellent material may be applied or printed in an area where the biologically active substance is not provided.

The sheet 10 may be formed with a stretchable film. For example, synthetic rubber such as silicone rubber, natural rubber, latex, a polyolefin film such as of polyethylene, polymethylpentene or a paraffinic film can be advantageously employed. The biologically active substance can be liberated and dissolved in the culture liquid by contacting the wall-shaped structure, formed on the cell culture plate, so as to surround the area on the sheet 10 where the biologically active substance is provided, and depressing the sheet from the rear surface until such area comes into contact with the culture liquid. In such case, a stretchable or elastic sheet is preferable as it provides a satisfactory adhesion thereby avoiding the leakage of the liquid.

A chemical treatment or an electrostatic treatment may be applied to the biologically active substance or to the sheet, in order that the biologically active substance 12 on the sheet 10 can be easily liberated from the sheet. For transferring the biologically active substance from the sheet to the culture liquid, after the sheet is adhered to the wall structure on the cell culture plate 2 and the cell culture plate and the sheet are shaken in such a manner that the culture liquid comes into contact with the area where the biologically active substance is provided, or the sheet is pressed with a rod-shaped article from the above thereby contacting the area holding the biologically active substance with the culture liquid (FIG. 7A). Also for efficient liberation, a vibration may be applied to the culture liquid or to the sheet. Also the transfer sheet may have a holding layer, for carrying the biologically active substance, on the sheet base. In this manner, it is possible to stably hold the biologically active substance. Also the sheet may have a recess for carrying the biologically active substance, which may be provided in such a recess. Also the sheet may be provided with a protruding wall-shaped structure, which surrounds each area or an area group constituting of two or more areas. Such configuration can facilitate positioning of a liquid droplet, provided by liquid discharge means. Furthermore, the sheet may be provided with a protruding portion, and the biologically active substance may be provided thereon. In such a case the biologically active substance can be easily contacted with the culture liquid and can be transferred thereto.

Formation of a recess, a protruding wall-shaped structure, or a protruding portion on the transfer sheet can be achieved for example by an injection molding, a pour molding, an adhesion of a chip by thermal fusion or with an adhesive material, or a press molding with a metal mold.

The biologically active substance 22 immobilized on the cell culture plate 2 and the biologically active substance 12 provided on the transfer sheet 1 may be constituted of the same biologically active substances, or different biologically active substances, or some of the biologically active substances are the same.

The cell culture plate 2 and the transfer sheet 1, described above, can be prepared in the following manner. First, a base 20 and a sheet 10 may be subjected to the treatment mentioned above if necessary. More specifically, the base 20 and the sheet 10 are washed to eliminate undesired substances and may be subjected to various chemical or physical treatments such as UV irradiation or a corona discharge. Also for the cell culture plate, it is possible, if necessary, to apply a polymer material or a silane coupling agent on the base 20 or a part thereof.

A treatment for facilitating carrying of the biologically active substance may be applied to the sheet 10. For such a treatment, a biologically active substance-holding layer may be formed on the entire surface of the sheet. For this purpose, there can be advantageously employed, for example, methyl cellulose, ethyl cellulose, hydroxypropyl cellulose, hydroxypropyl methyl cellulose, hydroxypropyl methyl cellulose phthalate, cellulose acetate phthalate, polyvinylpyrrolidone, macrogol, polyvinyl alcohol, polyacrylic acid, polymethacrylic acid, a methacrylic acid copolymer, a starch derivative such as starch, hydroxyethyl cellulose, sodium alginate, sodium celluloseglycollate, or sodium starchglycollate, a natural polymer such as dextrin, gum Arabic, carrageenan, agar, gelatin, tragacanth or crystalline cellulose, or a water-soluble compound such as glucose, sucrose, fructose, or xylitol. Such material may be coated on an entire or partial surface of the base 20, according to the necessity.

By suitably selecting the configuration of the holding layer, it is possible to attain a controlled release property in the biologically active substance, attached to the holding layer, into a culture liquid. Such controlled release property may also be achieved by adding, at the providing of the biologically active substance to the sheet, a substance capable of realizing a controlled release property (for example a water-soluble styrene-acrylic resin) to a liquid containing the biologically active substance. An amount of the substance for realizing the controlled release property is 10 mass % or less, preferably 5 mass % or less, to the liquid containing the biologically active substance.

The holding layer can be formed on the sheet 10 by dissolving or dispersing the aforementioned material in a suitable solvent to prepare a coating liquid, and coating such coating liquid on the sheet to form a coating film thereon. The coating can be carried out for example by a roll coating, a blade coating, an air knife coating, a gate roll coating, a bar coating, a size press, a spray coating, a gravure coating, a curtain coating, a screen printing, a flexographic printing or an offset printing. The thickness of the holding layer can be arbitrarily selected, but is preferably about 1 to 100 µm.

A biologically active substance 22 is depositing on such base 20 and on the sheet 10. Liquid discharge means can be advantageously employed for depositing. The liquid discharge means is capable of discharging a liquid droplet of a volume of 100 nl or less per drop, more specifically 1 nl or less, such as a micropipette, a microdispenser, or a discharge apparatus of ink jet method. A discharge apparatus of ink jet method can be employed particularly advantageously because the discharge apparatus is available inexpensively and a small liquid droplet can be discharged. Furthermore, among the ink jet methods, a thermal ink jet method and a piezo ink jet method can be employed advantageously. A discharge apparatus of the thermal ink jet method, being easy in preparation of fine discharge ports, can discharge a liquid containing a biologically active substance 22 at a high density. Also a discharge apparatus of the piezo ink jet method, in which a discharge energy is generated by a displacement of a piezoelectric element, can discharge the biologically active substance without giving a thermal stress thereto.

At the use of the liquid discharge means, the biologically active substance 22, 12 is dissolved in an appropriate solvent for discharge. An amount of the dissolved biologically active substance is 10 mass % or less, preferably 5 mass % or less. Any solvent may be employed as long as it can stably dissolve the biologically active substance 22 or 12, but water is employed advantageously. Water is employed in 30 mass % or higher, preferably 50 mass % or higher. As the water, there are preferably employed ion-exchanged water (deionized water) or various buffers for stably dissolving the biologically active substance 22, 12.

Also the aforementioned water-soluble solvent may be employed if necessary.

Also a liquid of the invention containing at least the biologically active substance 22 or 12 may contain at least a hydrophilic resin, in addition to the aforementioned components. The hydrophilic resin can be, for example, a natural polymer such as a ligninsulfonic acid salt or shellac, a styrene-acrylic acid-acrylate alkyl ester copolymer salt such as a polyacrylic acid salt, a styrene acrylic acid copolymer salt, or a styrene-acrylic acid-acrylate ester copolymer salt, an anionic polymer such as a styrene-maleic acid copolymer salt, a styrene-maleic acid-acrylate alkyl ester copolymer salt, a styrene-maleic acid half ester copolymer salt, a styrene-methacrylic acid copolymer salt, a vinylnaphthalene-acrylic acid copolymer salt, a vinylnaphthalene-maleic acid copolymer salt, a β-naphthalenesulfonic acid-formaline condensate salt, or polyphosphoric acid, polyvinyl alcohol, methylolated melamine, polyvinylpyrrolidone, or a cellulose derivative such as methyl cellulose, hydroxymethyl cellulose or carboxymethyl cellulose. In the present invention such resins may be employed singly or in a mixture of two or more kinds. Also there are many other materials, for example a natural resin such as albumin, gelatin, casein, starch, cationized starch, gum Arabic, and sodium alginate. An amount of the hydrophilic resin is 10 mass % or less, preferably 5 mass % or less. Naturally the present invention is not limited to such examples.

Such hydrophilic polymer compound can be added also in case of releasing the biologically active substance 22 from the transfer sheet with a controlled release property.

Also the liquid of the present embodiment containing at least the biologically active substance 22 or 12 may further include, if necessary for obtaining desired physical properties, a surfactant, a defoamer, an antiseptic, an inorganic salt, an organic salt and the like.

On the cell culture plate, after the biologically active substance 22 is provided by the liquid discharge means in a desired position on the base 20, the biologically active substance 22 is immobilized thereto. For immobilizing the biologically active substance 22 to the base 20, a treatment necessary for immobilization may be applied to the biologically active substance 22 or to the plate. The biologically active substance 22 may be treated to introduce therein a functional group necessary for covalent coupling, such as an amino group, a carboxyl group, a disulfide group, an epoxy group, a carbodiimide group, or a maleimide group, or to bond a chargeable material necessary for coupling by an electrostatic attractive force, such as fine particles of a metal or an inorganic oxide, a cationic or anionic polymer. Avidin or biotin, or an antigen molecule or an antibody molecule can be introduced for a biological affinity coupling. It is also possible to coat the substrate surface with a polymer material or a silane coupling agent and to introduce a functional group necessary for covalent bonding, such as an amino group, a carboxyl group, a disulfide group, an epoxy group, a carbodiimide group, or a maleimide group. It is also possible to form a conductive or semiconductive layer for charging the substrate surface on the substrate surface, for example, using a metal such as gold, silver, platinum or iron, an inorganic oxide such as indium tin oxide, titanium oxide or zinc oxide, or a conductive polymer such as polyacetylene, polypyrrole, polyaniline or polythiophene. It is also possible to provide the surface of the base 20 with a material having a binding ability with the material introduced into the biologically active substance 22, such as biotin or avidin, an antibody or antigen, or a protein having an antibody0binding ability such as protein A. Introduction of such materials provides a firm coupling between the surface of the base 20 and the biologically active substance 22.

At the immobilization, energy may be applied from the exterior, such as light radiation or heating. Such energy from the exterior allows to accelerate the coupling between the surface of the base 20 and the biologically active substance 22.

The cell culture plate 2 and the transfer sheet 1 can be prepared as described above.

The screening plate 2 and the transfer sheet 1 thus prepared can be stored in a container over a prolonged period. A more preferable stable storage can be achieved by sealing the transfer sheet in the container together with a drying agent or an oxygen removing agent. Also they can be more simply laminated with a plastic film.

In the following, there will be explained a method of cell culture with the cell culture kit constituted of the cell culture plate 2 and the transfer sheet 1 described above. By culturing cells with such kit, the cells are cultured under various influences by the biologically active substances. Prior to the cell culture, the transfer sheet and the cell culture plate may be sterilized if necessary for example by radiation or UV irradiation or by washing with alcohol. This operation will prevent an inhibition of the culture for example by undesired microorganisms.

Also in the cell culture with the cell culture kit of the cell culture plate 2 and the transfer sheet 1, the transfer sheet may be immersed in the culture liquid during the culture, or may be removed in the course of the culture. Also a desired substance may be added to the culture liquid of a desired area after the cell culture for a predetermined period. In this manner it is possible to control the concentration of the biologically active substance to the cells, to add an active substance, to vary the influences or to vary the adhesion to the plate. For adding a desired substance to the culture liquid, there can be employed a method contacting plural sheets with the culture liquid at different times. It is also possible, in the course of the culture, to replace the culture liquid and to use a different transfer sheet. In this manner, biologically active substances of a different combination can be applied at an arbitrary timing of the culture and the culture conditions can be easily changed. Also in the screening after the cell culture, a desired substance such as an indicator may be added in desired wells. In this manner the screening can be carried out easily.

Also the cultured cells may be removed from the cell culture plate during or after cell culture. In this manner the removed cultured cells may be utilized as an artificially prepared tissue or a part thereof. More specifically, the cultured cells can be removed by treating the cell culture vessel with trypsin after the cell culture. In this manner, the plate can be re-used. Such re-use of the plate is one of the advantages obtained by immobilizing the biologically active substance to the plate in such a manner that cells cannot incorporate the activating substance into a metabolic system. Also by coating the plate in advance with a temperature-responsive polymer such as poly(N-isopropylacrylamide) and executing the cell culture thereon, it is possible to remove the cultured cells by bringing the temperature to about 30° C., thereby causing a change in the hydrophilicity of the polymer surface. In this manner the cells can be utilized for example in a live tissue.

In the following there will be explained a screening method in which cells are cultured by using the cell culture kit comprised of the cell culture plate 2 and the transfer sheet 1, with a substance immobilized on the plate and a substance dissolved from the sheet into the culture liquid. As screening means, there can be utilized the aforementioned method of observing the morphological change of the cells cultured on the cell culture plate 2. For this purpose, there may be employed any microscope capable of observing the shape of the cells, not only an optical microscope but also a scanning electron microscope, a transmission electron microscope, a scanning probe microscope or a fluorescence microscope. A screening plate bearing cultured cells is placed in an observing position of such microscope and the shape of the cells is observed under the microscope. Microscopic observation of the cell morphology alone is sufficient for screening, enabling simple evaluation. The cells may be stained for evaluation. Cell staining facilitates evaluation under the microscope in case the cells proliferates in a high density or in case the cells causes a fusion by differentiation thereby forming a polykaryocyte.

Alternatively, there may be utilized a quantitative determination of a substance produced by the cells or incorporated therein in the course of or as a result of cell adhesion to the culture plate or proliferation or differentiation. In case an object of quantitative determination cannot be directly evaluated, the quantitative determination may be carried out with a reporter substance. As a specific example, a desired protein can be quantitatively measured by introducing a gene of a measurable protein in the vicinity of the gene of the desired protein to be measured by the genetic engineering technology, and by quantitatively determining the expressed measurable protein. Evaluation of such substances allows a detailed survey of changes in the cells induced by the substance immobilized on the base, and leads to elucidation of the information transmission mechanism in the cells. In case of carrying out evaluation with a substance incorporated into the cells, it is also possible to label the substance with a labeling material enabling evaluation, whereby the quantitative determination becomes rather easy.

For a quantitative determination of these substances, there may be employed a method of measuring an amount of a radiation emitted from a radioactive compound, a method of measuring an amount of fluorescence emitted from a substance labeled with a fluorescent substance, a method of measuring an amount of light emitted from a light-emitting substance, or a method of measuring an optical absorbance of a dye.

A method that employs a radioactive compound containing a radioactive isotope of an element abundantly present in a live tissue such as hydrogen, carbon, nitrogen, phosphor or sulfur and measures the intensity of radiation from such a compound is highly sensitive, and allows observation of phenomena occurring in a live body, because such a hot compound has the same chemical properties as the cold compound.

Also a method of labeling with a fluorescent substance is relatively simple and gives little influence on the metabolism of the cells by employing a fluorescent substance of a low molecular weight. Also in a quantitative determination of a substance produced by the cells by a determination method utilizing an antigen-antibody reaction, an evaluation by a fluorescent measurement is effective since antibodies labeled with a fluorescent substance are available in various kinds and provide a high measuring sensitivity.

Also the method of measuring luminescence from a luminescent substance allows to recognize even a small change, since the luminescence can be measured with a high sensitivity. When a gene expressed with cell adhesion, proliferation, differentiation or substance production caused by a substance has been specified, it is possible to introduce a firebug luciferase gene or the like in the vicinity of such a gene and an amount of luciferase produced by the gene expression is measured from the intensity of luminescence generated on addition of ATP and luciferin. In this manner it is possible to evaluate the influence of the screened substances from the luminescence intensity.

In a method of measuring the optical absorbance of a dye, it is possible to amplify the optical absorbance of a dye for example by employing an enzyme reaction in combination, thereby enabling a quantitative determination of a substance of a very small amount.

EXAMPLES

In the following, the present invention will be clarified further by examples thereof, but such examples are merely given for the purpose of deeper understanding of the invention and the present invention is not limited to such examples.

Example 1

The following method was employed for mixing one or more biologically active substances in combination into a cell culture liquid. Basic fibroblast cell growth factor (b-FGF), insulin-like growth factor (IGF-I) and bone morphogenetic protein (BMP-2) were used as the biologically active substance. b-FGF was dissolved in a physiological saline solution, IGF-I in 10 mM acetic acid, and BMP-2 in 4 mM hydrochloric acid to prepare solutions each containing the biologically active substance at a concentration of 20 µg/ml and 5% glycerin. Ink cartridges were washed with 70% ethanol, to which the respective solutions prepared above were filled.

Then, on a base of a polyolefin sheet (NOVIX-II® manufactured by Asahi Techno Glass), sterilized in advance with a sterilizing lamp, the biologically active substances were discharged by using an ink jet printer (Ink jet printer F930, Canon). The amount of the biologically active substance was controlled by the printing area and the number of discharge, and 27 areas different in kinds and concentrations of the biologically active substances were formed on the transfer sheet by superimposed discharge.

A DMEM (Dulbecco's modified Eagle's minimum essential medium) culture medium containing 2% FBS (fetal bovine serum) was put in wells of a 96-well transparent microplate (SUMILON for cell culture).

The transfer sheet was tightly placed on the microplate in such a manner that the 27 areas corresponded to the wells of the microplate, and they were lightly shaken to make the culture liquid contact with the transfer sheet and dissolve the biologically active substances into the culture liquid. Then, in each well, cells of mouse skeletal muscle cell strain C2C12 were cultured for 96 hours at 37° C., in humidified air supplied with 5% $CO_2$.

Microscope observation of the microplate after the culture showed cell proliferation in the areas containing b-FGF, differentiation into muscle cells in the areas containing IGF-I, and differentiation into bone cells in the area containing BMP-2, respectively accelerated depending on the concentrations.

The cells after the culture were treated with 10% formalin for 15 minutes and then with methanol for 15 minutes, and finally with a 1000-fold dilution of fluorescent dye (TOTO-3 manufactured by Molecular Probe) for 30 minutes for fluorescent staining of DNA. The fluorescent intensity of TOTO-3 at 700 nm was employed as an index for the cell proliferation. Also the cells were subjected to freeze-fracture and the creatinkinase (KP) and alkaliphosphatase (ALP) activities were measured. Relative activity thereof based on the total protein content in the solution was taken as an index of differentiation, i.e., the KP activity for muscle differentiation and the ALP activity for bone differentiation.

As a result, it was shown that, in areas where the three factors were present in various concentrations, the cell differentiation proceeded in a different direction compared with areas where only one factor was present. Use of such a transfer sheet allows to investigate the interaction of plural biologically active substances at the same time.

Example 2

The following process was employed for investigating the influences of biologically active substances on cells when the species and concentrations of the active substances were varied in a predetermined period.

As the biologically active substances, fibroblast cell growth factor-2 (FGF-2), insulin-like growth factor-I (IGF-I), bone morphogenetic protein-2 (BMP-2) and transforming growth factor-β (TGF-β) were employed. Solutions of these biologically active substances were prepared and filled in ink cartridges as in Example 1.

Then, two polyolefin sheets (NOVIX-II® manufactured by Asahi Techno Glass) were coated with polyvinyl alcohol (Gosenol GM14L, manufactured by Nippon Gosei Kagaku) by using a bar coater to a dry film thickness of 5 μm, thereby preparing two sheet bases having a holding layer. Then, the sheets were sterilized with a sterilizing lamp and the biologically active substances were discharged onto them using an ink jet printer. Thus two transfer sheets were prepared, a transfer sheet A having FGF-2 and IGF-I in various combinations and concentrations in 12 areas, and a transfer sheet B having BMP-2 and TGF-β in various combinations and concentrations in 12 areas.

A DMEM culture liquid containing 2% FBS was put into wells of two 96-well transparent microplates 1 and 2. After the transfer sheets A and B were attached onto the microplates 1 and 2 respectively as in Example 1, the biologically active substances were dissolved by pushing each area carrying the biologically active substances from the back of the sheet with a rod (FIG. 5). In this manner, the sheet A was used to provide FGF-2 and IGF-I to the microplate 1, and the sheet B was used to provide BMP-2 and TGF-β to the microplate 2. Then, in each well of each microplate, cells of mouse skeletal muscle cell strain C2C12 were cultured for 48 hours in humidified air supplied with 5% $CO_2$. 48 hours after the start of the culture, the culture liquid was removed from each cell by suction. After fresh 2% FBS/DMEM was added to each well, a transfer sheet B was applied to the microplate 1 to supply BMP-2 and TGF-β, while a transfer sheet B was applied to the microplate 2 to supply FGF-2 and IGF-I, and the cell culture was conducted for further 48 hours. After the culture, cells were frozen and disrupted and CK and ALP activities thereof were measured to use relative activities as indexes for muscle differentiation and bone differentiation respectively.

As a result, muscle differentiation was accelerated in areas containing IGF-I only, and bone differentiation was accelerated in areas containing BMP-2 only. It was confirmed that, when four factors acted on the cells in various combinations and concentrations in a time sequential manner, the cell differentiation proceeded differently in comparison with cases where these factors acted at the same time.

Use of such transfer sheets allows to change the kinds and the concentrations of the substances acting under plural conditions within a predetermined time.

Example 3

The following process was employed for investigating the influences of biologically active substances on cells when the species and concentrations of the active substances were varied in a predetermined period and active substances were gradually released.

As the biologically active substances, there were employed bone morphogenetic protein (BMP-2), fibroblast cell growth factor (FGF-2), and insulin-like growth factor (IGF-I). The BMP-2 and FGF-2 were respectively prepared into 20 μg/ml solutions containing 5% glycerin. On the other hand, the 20 μg/ml solution of the insulin-like growth factor (IGF-I) contained 5% glycerin and 3% styrene-acrylic resin monoethanolamine salt (average molecular weight 8,000, acid value 250) for controlled release of IGF. Ink cartridges were washed with 70% ethanol, and were filled with the respective solutions of the biologically active substances.

Then, a plurality of transfer sheets each containing a single biologically active substance in four different concentrations were prepared by providing on a base of a polyolefin sheet the respective biologically active substance using an ink jet printer as in Example 1. Each polyolefin sheet was processed in advance to have minute holes at positions corresponding to the wells of a 96 well plate to allow gas exchange. A DMEM culture liquid containing FBS by 2% was put in wells of five 96-well transparent microplates. Then the transfer sheet carrying BMP-2 was placed on each of the 96-well transparent microplates to superimpose on the wells of the microplate.

The sheet was pressed from the above using a jag having 96 protrusions at positions corresponding to the wells of the microplate, so that each region of the sheet came in contact with the culture liquid in each well to dissolve BMP-2 into the culture liquid. Then, in each well, cells of a mouse skeletal muscle cell strain C2C12 were added. Next, a transfer sheet carrying IGF-I was superimposed on each of the microplate and pressed from the above using the above jig so that each region of the sheet came in contact with the culture liquid in each well to gradually release IGF-I into the culture liquid, and cell culture was started. The above operations were carried out in the same manner with the five microplates. After a predetermined time from the start of the culture, the transfer sheet of one of the microplates was replaced by a transfer sheet carrying FGF-2 to dissolve FGF-2 into the culture liquid. After that the transfer sheet was replaced by the previous IGF-I sheet and the culture was continued. All the cells were cultured for 114 hours in total at 37° C., in humidified air containing 5% $CO_2$. The FGF-2 addition was conducted at the following points:

(1) immediately after the start of culture;
(2) 12 hours after the start of culture;
(3) 24 hours after the start of culture;
(4) 48 hours after the start of culture;
(5) 72 hours after the start of culture.

The cells after the culture were treated with 10% formalin for 10 minutes and staining with the enzyme activity of alkaliphosphatase (ALP) was carried out as an index for bone differentiation by BMP-2.

As a result, the influence on the bone differentiation changed by the timing of action of EGF-2 under sustained release of the insulin-like growth factor-I (IGF-I). In the case without addition of FGF-2 and in the aforementioned conditions (3), (4) and (5), portions stained with ALP were confirmed, but the stained portions were scarcely observed in (1) and (2). These results indicate that, at the differentiation from the muscle cells into bone cells, the bone differentiation is significantly suppressed by adding FGF-2 within 24 hours after the start of the culture. It is thus possible, by transfer sheets capable of adding the biologically active substance at different times, to investigate the effect of the action period and the effect of controlled release.

Example 4

In this example, potential allergens provided on transfer sheets were transferred to a culture liquid, in which cells were cultured to quantitatively determine histamine, an inflammation-inducing substance produced by sensitive cells, thereby evaluating whether a subject has an allergy. This example evaluated allergy to cedar pollen, cow milk, house dust and ambrosia. The cedar pollen, house dust and ambrosia were sufficiently ground in advance with a homogenizer. An aqueous solution containing each allergen was centrifuged, and a soluble component was obtained by eliminating a precipitate. Then the solution of each soluble allergen component was diluted with 50% methanol into a concentration of 50 μg/ml, and a transfer sheet was prepared by forming 4 areas of respective allergen components and 6 areas of two allergen combinations of the four allergens on a 20 μm thick polyester film using an ink jet printer. The blood sample of an object person were subjected to a density gradient centrifugation to separate blood components, thereby obtaining allergy-reactive cells.

A DMEM culture liquid containing FBS (fetal bovine serum) by 10% was put into wells of a 12-well transparent microplate. The transfer sheet prepared above was placed on the 12-well transparent microplate such that areas were superimposed onto the wells of the microplate. The sheet and plate was lightly shaken to contact the culture liquid with the transfer sheet, thereby dissolving the biologically active substances in the culture liquid. Then, in each cell, the allergen reactive cells were cultured for 96 hours at 37° C., in humidified air containing 5% $CO_2$. The plate after culture was taken out and rinsed with an isotonic phosphate buffer. After a treatment with methanol for 30 minutes and drying, the cells were treated with a rabbit anti-histamine antibody for 1 hour, and washed with PBS followed by a treatment with an anti-rabbit Ig antibody labeled with horse radish peroxydase for 1 hour. Then a histamine amount was determined from an absorbance change of o-phenylenediamine using an enzyme-antibody process. As a result, histamine was found in a large amount in the area containing house dust alone, so that the person was considered allergic to the house dust. Also the result was negative for the cedar pollen, cow milk or ambrosia alone, but histamine was detected in an area where ambrosia and cow milk were combined, so that a possibility of allergy was identified in case of taking these two at the same time. In this manner, the transfer sheet can be used to diagnose the cause of allergy in a simple manner. In particular, as shown in this example, allergy reaction to a combination of plural allergens can be easily investigated.

Example 5

The following method was employed for acting biologically active substances in combination on cells. As the biologically active substances, there were employed basic fibroblast cell growth factor (b-FGF), insulin-like growth factor (IGF-I) and bone morphogenetic protein (BMP-2).

First, bFGF and IGF-I were immobilized onto a polystyrene 96-well cell culture plate in the following manner.

On the cell culture plate coated with poly-L-lysine, a solution (1.5 mg/ml) of active dextran activated with tresyl chloride was added to bind the activated dextran to the plate. Then carbonate buffer solutions containing b-FGF and IGF-I respectively were prepared, applied to the microplate with various amounts. The microplate was left to stand for 12 hours at 4° C. to prepare a cell culture plate including areas where b-FGF and IGF-I were immobilized either singly or in combination with different concentrations, as well as control areas without immobilization.

A polystyrene sheet having projections corresponding the wells of the microplate was provided and sterilized. Then a solution containing 5% glycerin and 20 μg/ml BMP-2 was prepared and filled in an ink cartridge washed with 70% ethanol. Then BMP-2 was provided by using a Canon ink jet printer PIXUS950i onto the projections of the polystyrene sheet, thereby obtaining a transfer sheet.

A culture liquid DMEM containing FBS by 2% was put in the wells of the 96-well cell culture plate prepared above.

The transfer sheet was placed on the 96-well transparent microplate in such a manner that each projection made a pair with a well of the microplate and contacted with the wall of the well. Thus the area of the biologically active substance formed on each projection was brought into contact with the culture liquid, and BMP-2 was dissolved in the culture liquid with shaking for accelerating dissolution of the biologically active substance. Then cells of mouse skeletal muscle cell strain C2C12 suspended in DMEM (Delbucco's modified eagle's minimum essential medium) supplemented with 2% FBS (fetal bovine serum) were added to each well to 500 cells/well, and was cultured for 96 hours at 37° C., in humidified air containing 5% $CO_2$.

After the culture, the cell culture plate was observed under an optical microscope to show cell proliferation in areas containing b-FGF, muscle differentiation in areas containing IGF-I, and bone differentiation in areas containing BMP-2 depending on the concentration thereof. Then the cells were treated with 10% formalin for 15 minutes and then with methanol for 15 minutes, and reacted with a fluorescent dye for 30 minutes for fluorescent staining of DNA. Fluorescent intensity of DNA at 700 nm was measured as an index for cell proliferation. Also the cells were subjected to freeze-fracture to measure the creatinkinase (KP) and alkaliphosphatase (ALP) activities. Relative activity thereof based on the total protein content in the solution was taken as an index of differentiation, i.e., the KP activity for muscle differentiation and the ALP activity for bone differentiation. Thus the complex effects of three factors, namely immobilized bFGF, soluble IGF-I and BMP-2, to the cells were analyzed.

Example 6

An epidermal cell growth factor (EGF) and a nerve cell growth factor (NGF) were employed as the biologically active substances. A culture plate of polystyrene 96-well cell culture plate was prepared by a process similar to that in Example 5, providing areas (wells) where EGF was immobilized with stepwise concentrations, and control areas (wells) of no immobilization. Separately, a stretchable polyolefin sheet was coated with hydroxypropyl cellulose by using a bar coater and heated for 10 minutes at 60° C. to form a holding layer. Then EGF and NGF were provided on the sheet by using a Canon ink jet printer PIXUS950i to obtain a transfer sheet on which areas carrying EGF and NGF singly or in combination. Screening was conducted with these cell culture plate and transfer sheet.

The transfer sheet was placed on the cell culture plate sterilized in advance with a sterilizing lamp and filled with a culture liquid, then the areas carrying biological substance(s) of the sheet were brought into contact with the culture liquid in the wells by pushing the opposite surface of the sheet with a pointed article, and the contact was maintained for 15 minutes under light shaking to dissolve the biologically active substance in the culture liquid. Then cells of a nerve cell strain PC12 suspended in RPMI (Rosewell Park Memorial Institute) 1640 culture medium containing 2% FBS were added to each well to 500 cells/well, and cultured for 48 hours at 37° C., in humidified air containing 5% $CO_2$. Then the culture liquid was removed, and the cells were immobilized and stained with hematoxilin-eosin for evaluating the level of proliferation and differentiation, and the plate was observed under an optical microscope on the nuclei and cell morphology. As a result, it was confirmed that the EGF in an immobilized state affected the PC12 cells differently from that in a dissolved state. In this manner, effects of a growth factor in a dissolved state and an immobilized state on cells could be investigated in a simple manner.

Example 7

A rat was immunized with mouse bFGF as an antigen, and after two months the spleen cells were fused with myeloma cells to obtain hybridomas, from which a large number of monoclonal antibody producing hybridomas were obtained and 96 monoclonal antibodies were purified. Then, mouse bFGF was immobilized at 200 pg/mm² on a polystyrene 96-well plate to prepare a culture plate. Separately, a para film was coated with hydroxypropyl cellulose on the entire surface by using a bar coater, on which the obtained monoclonal antibodies were provided by using a Canon ink jet printer PIXUS950i at positions corresponding to the wells of the 96-well plate. 75 µl of DMEM culture medium was added to each well of the culture plate, and the sheet was placed on the culture plate, and the culture liquid in the well was brought into contact with the antibody area of the screening sheet, and the antibody was transferred into the culture liquid.

Then 75 µl of DMEM medium containing muscle cells of strain C2C12 at $6 \times 10^4$ cell/ml was added to each well, and cell culture was conducted at 37° C. in humidified air containing 5% $CO_2$. After 48 hours, 0.002% 5-bromo-2'-deoxyuridine (BrdU) was added to the culture liquid, after 3 hours the culture liquid was removed and the cells were treated with methanol for 30 minutes. Staining of the cells with an FITC labeled anti-BrdU antibody was conducted for evaluating cell proliferation, and the nuclei were stained with a 10,000-fold dilution of Hoechst 33258 for 5 minutes. The excessive staining solution was washed off with an isotonic phosphate buffer. Thus prepared plate was observed under a fluorescent microscope to evaluate the number of the stained nuclei. Also the number of nuclei containing BrdU-labeled DNA was determined by fluorescent analysis.

As a result, in three wells the fluorescence of BrdU was low in comparison with other wells showing that monoclonal antibodies A, B and C corresponding to these wells were neutralizing antibodies that efficiently inhibited the growth promoting effect of bFGF.

Example 8

In order to investigate the concentration dependence of the bFGF-inhibiting effect of the three neutralization antibodies obtained in Example 7, there was prepared a cell culture plate in which bFGF was immobilized at three different concentrations in the wells of a polystyrene 96-well plate. Separately, a parafilm was coated with hydroxypropyl cellulose on the entire surface by using a bar coater, on which the obtained monoclonal antibodies A, B and C were provided by using a Canon ink jet printer PIXUS950i at positions corresponding to the wells of the 96-well plate. 75 µl of DMEM culture medium was added to each well of the culture plate, and the sheet was placed on the culture plate, and the culture liquid in the well was brought into contact with the antibody area of the screening sheet, and each antibody was transferred into the culture liquid.

Then 75 µl of DMEM medium containing muscle cells of strain C2C12 at $6 \times 10^4$ cell/ml was added to each well, and cell culture was conducted at 37° C. in humidified air containing 5% $CO_2$.

After 48 hours, the culture liquid was removed, and the cells were treated with methanol for 30 minutes, dried and immobilized. For evaluating cell proliferation, the nuclei were stained with a 10,000-fold dilution of Hoechst 33258 for 5 minutes. The excessive staining solution was washed off with an isotonic phosphate buffer. Thus prepared plate was observed under a fluorescent microscope to evaluate number of the stained nuclei.

As a result, in the wells containing the transferred bFGF neutralizing antibody, the number of cells decreased with an increase in the concentration of each neutralizing antibody, indicating inhibition of the cell proliferation-accelerating effect of bFGF. Also the comparison of the cell numbers indicated that the strength of inhibition was in an order of B>C>A.

The present invention is not limited to the above embodiments and various changes and modifications can be made within the spirit and scope of the present invention. Therefore, to appraise the scope of the present invention, the following claims are made.

This application claims priority from Japanese Patent Applications No. 2003-418523 filed Dec. 16, 2003 and No. 2003-418535 filed on Dec. 16, 2003, which are hereby incorporated by reference herein.

The invention claimed is:

1. A cell culture kit comprising:
   a culture plate having two or more discrete culture regions for culturing a cell; and
   a sheet having covering portions discretely arranged to cover the respective culture regions,
   wherein each of the culture regions holds a first biologically active substance, and each of the covering portions holds a second biologically active substance, each of the first and second biologically active substances having a biological activity on a cell,
   wherein the sheet is made from an elastic or flexible film at least at the covering portions,
   wherein the first biologically active substance is immobilized on the culture regions, and the second biologically active substance is attached to the covering portions, and
   wherein the sheet constitutes a transfer sheet for transferring the second biologically active substance to the culture regions.

2. The cell culture kit according to claim 1, wherein the culture regions hold the first biologically active substance in different concentrations.

3. The cell culture kit according to claim 1, wherein the each of the culture regions is formed in a recess formed in the plate.

4. The cell culture kit according to claim 1, wherein each of the culture regions is surrounded by a protruding wall-shaped structure.

5. The cell culture kit according to claim 1, wherein a layer for holding the second biologically active substance is formed on an entire or partial surface of the sheet.

6. The cell culture kit according to claim 5, wherein the holding layer is able to release the second biologically active substance during cell culturing or the holding layer is able to sustainably release the second biologically active substance.

7. The cell culture kit according to claim 1, wherein each of the covering portions is formed in a recess formed in the sheet.

8. The cell culture kit according to claim 1, wherein each of the covering portions is formed on a protruding portion formed on the sheet.

9. The cell culture kit according to claim 1, wherein each of the covering portions is surrounded by a protruding wall-shaped structure formed on the sheet.

10. The cell culture kit according to claim 1, wherein the second biologically active substance is attached to the covering portions so as to be released when it is in contact with a culture liquid.

11. The cell culture kit according to claim 1, wherein the second biologically active substance is attached to each of the covering portions by discharging a liquid droplet containing the second biologically active substance.

12. A method of culturing a cell with a cell culture kit as defined in any one of claims 1 and 2 to 9, comprising a step of covering the culture regions on the culture plate with the covering portions of the sheet and a step of contacting a cell with a biologically active substance in a culture liquid in the culture regions.

* * * * *